(12) United States Patent
Hoenhause

(10) Patent No.: US 8,567,804 B1
(45) Date of Patent: Oct. 29, 2013

(54) MOBILE DEVICE FOR SUPPORTING A USER IN A STANDING, SITTING, OR KNEELING POSITION

(76) Inventor: Jody M. Hoenhause, Lisbon, ND (US)

( * ) Notice: Subject to any disclaimer, the term of this patent is extended or adjusted under 35 U.S.C. 154(b) by 288 days.

(21) Appl. No.: 13/115,173

(22) Filed: May 25, 2011

(51) Int. Cl.
B62M 1/00 (2010.01)
B60K 1/00 (2006.01)

(52) U.S. Cl.
USPC ............ 280/220; 180/65.1; 280/210; 280/29

(58) Field of Classification Search
USPC ......... 180/6.5, 11, 907, 65.1; 280/250.1, 647, 280/87.01, 87.041, 650, 210, 220, 29; 297/330, DIG. 4, DIG. 10
See application file for complete search history.

(56) References Cited

U.S. PATENT DOCUMENTS

| 4,437,537 A | 3/1984 | Ausmus |
| 4,456,086 A * | 6/1984 | Wier et al. ...................... 180/11 |
| 5,265,689 A | 11/1993 | Kauffmann |
| 5,366,036 A | 11/1994 | Perry |
| 5,458,349 A | 10/1995 | Mung-Tung |
| 5,556,121 A | 9/1996 | Pillot |
| 5,791,425 A | 8/1998 | Kamen |
| 6,125,957 A | 10/2000 | Kauffmann |
| 6,659,211 B2 | 12/2003 | Esposito |
| 6,685,658 B1 * | 2/2004 | Dietz et al. ....................... 601/5 |
| 2010/0207353 A1 | 8/2010 | Hsu |

* cited by examiner

*Primary Examiner* — John Walters
*Assistant Examiner* — James Triggs
(74) *Attorney, Agent, or Firm* — Neustek Law Offices

(57) ABSTRACT

A mobile device for supporting a user in a standing, sitting, or kneeling position such as to increase the mobility of paraplegic persons or other users incapable of moving as desired. The mobile device includes a drivable base having wheels and/or track members, a platform pivotally connected to the base and movable from a horizontal position to a forwardly-angled position, an actuator connected to the platform for angular adjustment of the platform, a pair of leg supporting assemblies connected to the platform and being hinged along a lengthwise axis, a pair of actuators connected to the leg supporting assemblies for pivoting the leg supporting assemblies, and a securing assembly connected to the leg supporting assemblies for securing a user to the device. The device also includes a wireless handheld controller for operating the drive unit and actuators.

18 Claims, 7 Drawing Sheets

MOBILE DEVICE FOR SUPPORTING A USER IN A STANDING, SITTING, OR KNEELING POSITION

CROSS REFERENCE TO RELATED APPLICATIONS

Not applicable to this application.

STATEMENT REGARDING FEDERALLY SPONSORED RESEARCH OR DEVELOPMENT

Not applicable to this application.

BACKGROUND OF THE INVENTION

1. Field of the Invention

The present invention relates generally to a mobile device and more specifically it relates to a mobile device for supporting a user in a standing, sitting, or kneeling position such as to increase the mobility of paraplegic persons or other users incapable of moving as desired.

2. Description of the Related Art

Any discussion of the related art throughout the specification should in no way be considered as an admission that such related art is widely known or forms part of common general knowledge in the field.

Persons confined to wheelchairs may become uncomfortable, stressed, or depressed due to long periods of sitting. Wheelchairs do not permit an occupant to stand and may be difficult to maneuver, especially in confined, crowded, or off-road situations. In addition, it may be beneficial for a user to stand in certain situations, such as when in a crowded location, or to offer a better viewpoint. Prior mobile devices such that permitted a user to stand suffer various drawbacks, such as not being suited for off-road use, not permitting the user to kneel, and being overly large such as to restrict maneuverability. Because of the inherent problems with the related art, there is a need for a new and improved mobile device for supporting a user in a standing, sitting, or kneeling position such as to increase the mobility of paraplegic persons or other users incapable of moving as desired.

BRIEF SUMMARY OF THE INVENTION

A system to increase the mobility of paraplegic persons or other users incapable of moving as desired. The invention generally relates to a mobile device which includes a drivable base having wheels and/or track members, a platform pivotally connected to the base and movable from a horizontal position to a forwardly-angled position, an actuator connected to the platform for angular adjustment of the platform, a pair of leg supporting assemblies connected to the platform and being hinged along a lengthwise axis, a pair of actuators connected to the leg supporting assemblies for pivoting the leg supporting assemblies, and a securing assembly connected to the leg supporting assemblies for securing a user to the device. The device also includes a wireless handheld controller for operating the drive unit and actuators.

There has thus been outlined, rather broadly, some of the features of the invention in order that the detailed description thereof may be better understood, and in order that the present contribution to the art may be better appreciated. There are additional features of the invention that will be described hereinafter and that will form the subject matter of the claims appended hereto. In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

Figure 1:
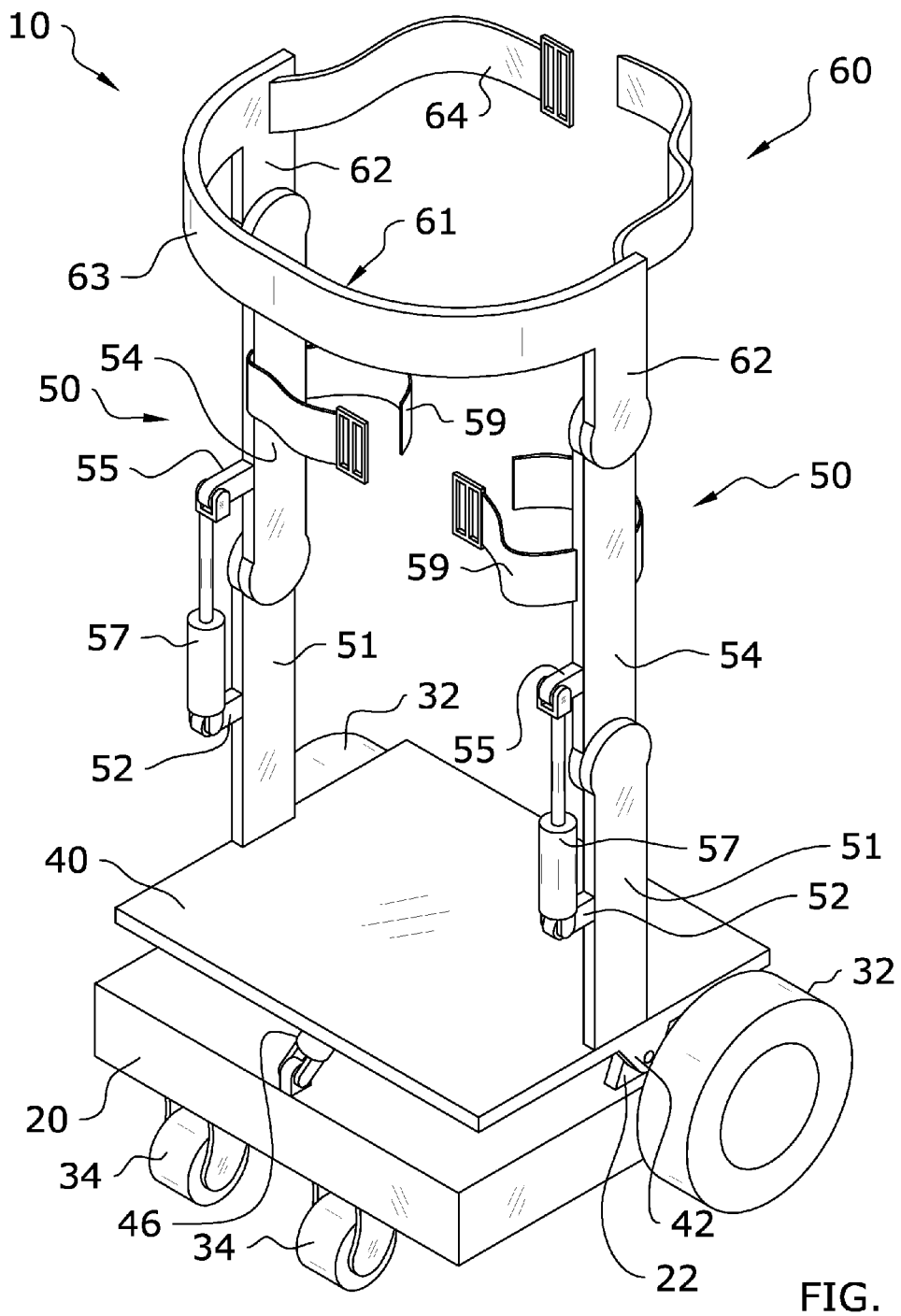
FIG. 1 is an upper perspective view of the present invention.
Figure 2:
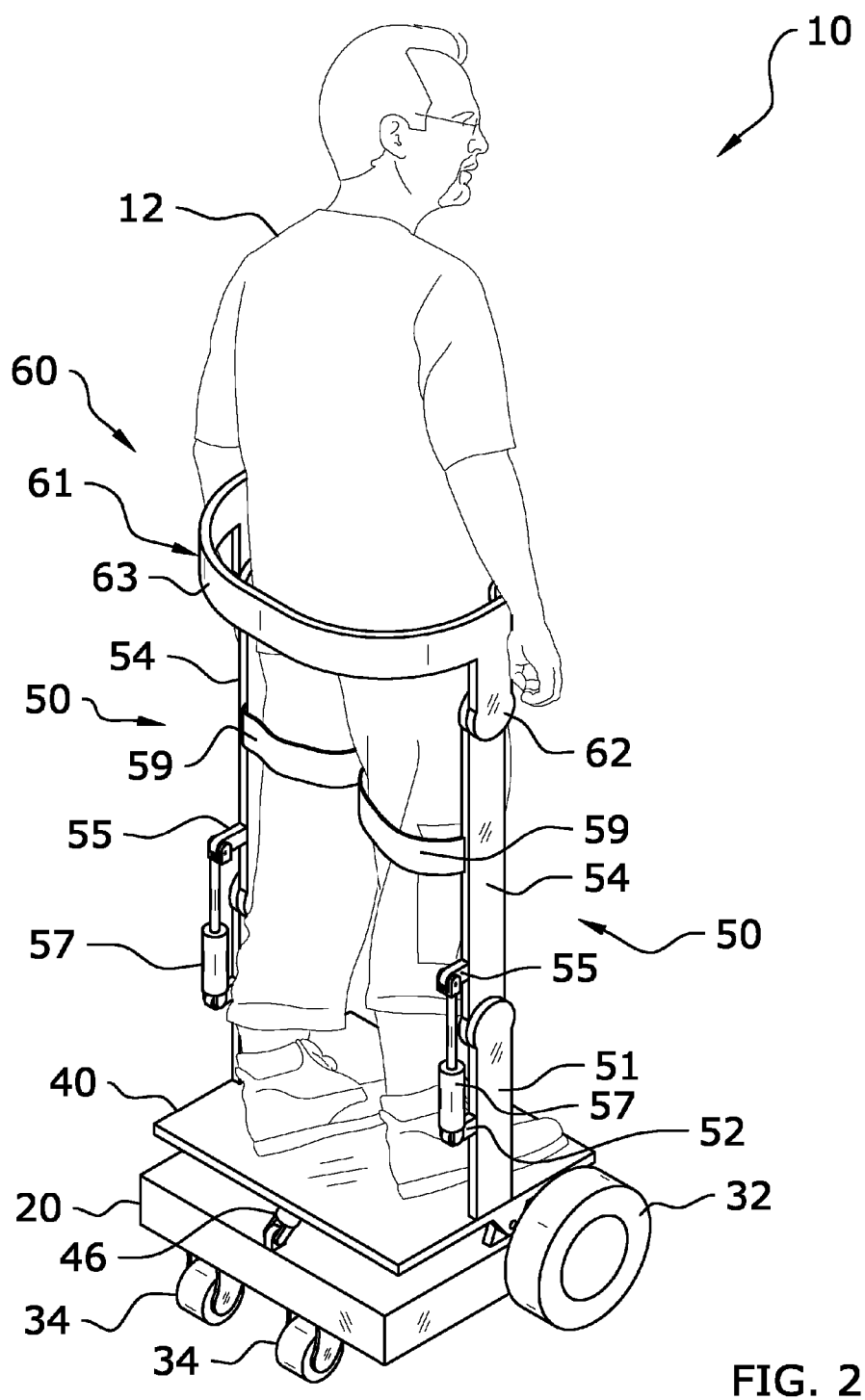
FIG. 2 is an upper perspective view of the present invention with a user secured therein.

A. Overview.

Turning now descriptively to the drawings, in which similar reference characters denote similar elements throughout the several views, FIGS. 1 through 7 illustrate a mobile device for supporting a user in a standing, sitting, or kneeling position 10, which comprises a drivable base 20 having wheels 32, 34 or 37, 38 and/or track members 36, a platform 40 pivotally connected to the base 20 and movable from a horizontal position to a forwardly-angled position, an actuator 46 connected to the platform 40 for angular adjustment of the platform 40, a pair of leg supporting assemblies 50 connected to the platform 40 and being hinged along a lengthwise axis, a pair of actuators 57 connected to the leg supporting assemblies 50 for pivoting the leg supporting assemblies 50, and a securing assembly 60 connected to the leg supporting assemblies 50 for securing a user 12 to the device. The device also includes a wireless handheld controller 70 for operating the drive unit 30 and actuators 46, 57.

B. Base and Drive Unit.

The base 20 may be of various sizes and materials. Preferably the base 20 is comprised of a size at least as large as the feet of the user 12 and comprised of a material suitable for holding the weight of the user 12. The preferred embodiment illustrates a square or rectangular shaped base 20 supported within a horizontal plane; however other suitable configurations may be utilized.

The mobile device 10 includes a drive unit 30 generally comprised of a motor and components for transferring a rotational force to the drive wheels 32. The drive unit 30 may be embedded within the base 20 or attached to the base 20 or other element of the mobile device 10. The motor of the drive unit 30 is generally of an electric type; however other fuel-powered motors may be utilized as well.

The drive unit 30 generally rotatably drives a pair of drive wheels 32 extending from opposing sides of the base 20. The mobile device 10 may also include a pair of idler wheels 34 having a caster wheel structure such as to rotate and swivel, or may alternately or additionally include more drive wheels. The drive wheels 32 may rotate simultaneously or separately such as to permit forward, rearward, or zero-radius turning of the base 20 and mobile device 10. The preferred embodiment illustrates drive wheels 32 comprised of a greater diameter than the idler wheels 34; however the diameter of the drive wheels 32 and idler wheels 34 may be altered as appreciated.

Figure 3:
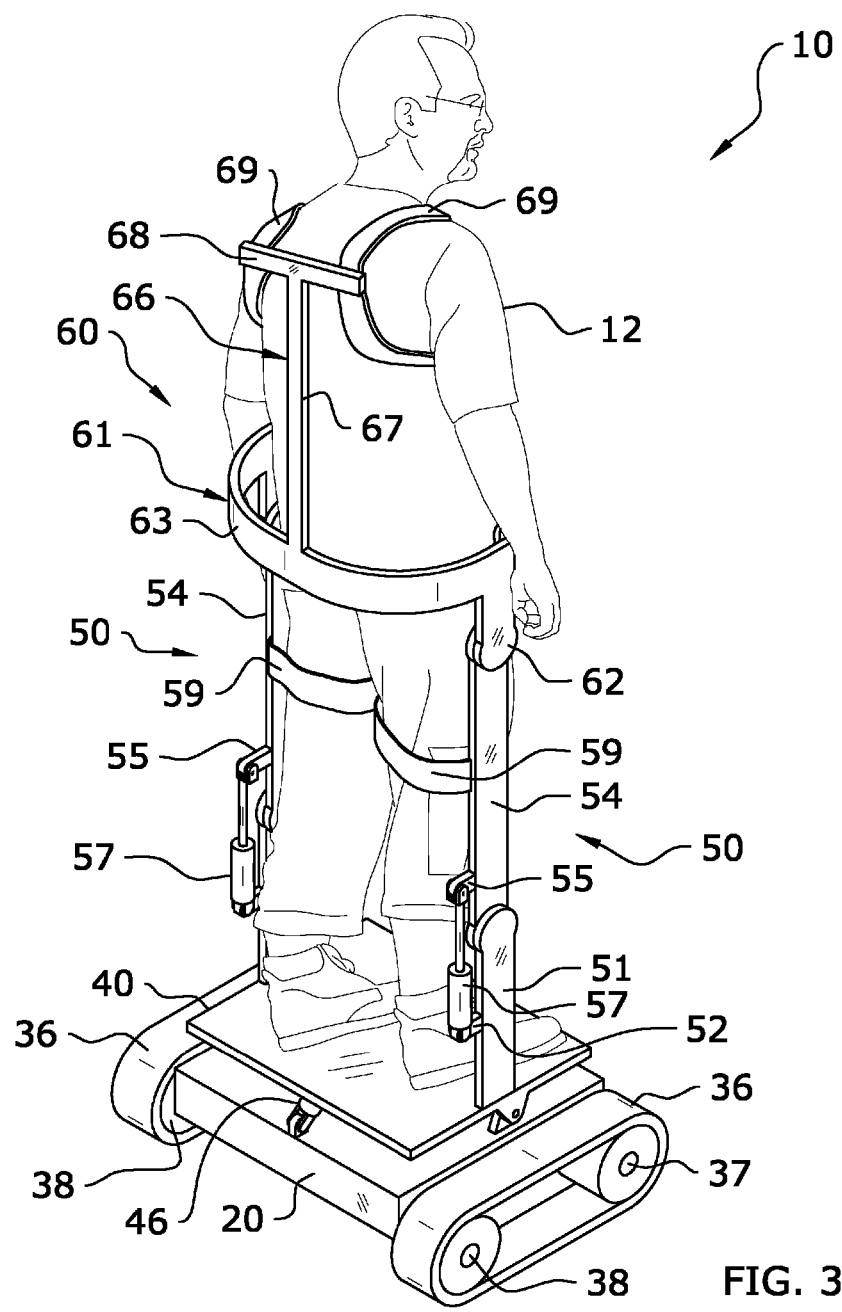
FIG. 3 is an upper perspective view of the present invention with a user secured therein and having track members and the back support.

The mobile device 10 may also have track members 36 mounted thereon such as to circulate around front and rear wheels 37, 38 as illustrated in FIG. 3. The track members 36 may have various grips, lugs, or traction members thereon to permit for the mobile device 10 to travel upon mud, snow, or other terrain generally classified as off-road terrain. The track members 36 are supported via at least front and rear wheels 37, 38, one or more of which may be rotatably driven by the drive unit 30. It is appreciated that more wheels may be utilized if needed to support the track members 36.

C. Platform.

The user 12 stands upon the upper surface of the platform 40 and thus the platform 40 is supported above the base 20 as illustrated in FIGS. 2 through 6. The platform 40 is further preferably comprised of a similar shape as the base 20. The platform 40 is further pivotally connected to the base 20 such as to permit for pivotal adjustment to a horizontal position and to a forwardly-angled position. It is appreciated that in certain circumstances, the platform 40 may pivot rearwardly.

The platform 40 includes a downwardly extending connector 42 that pivotally connects with an upwardly extending connector 22 of the base 20 such as to permit the platform 40 to pivot with respect to the base 20. The connectors 22, 42 are preferably positioned upon each side of the base 20 and platform 40 to support each side.

Figure 5:
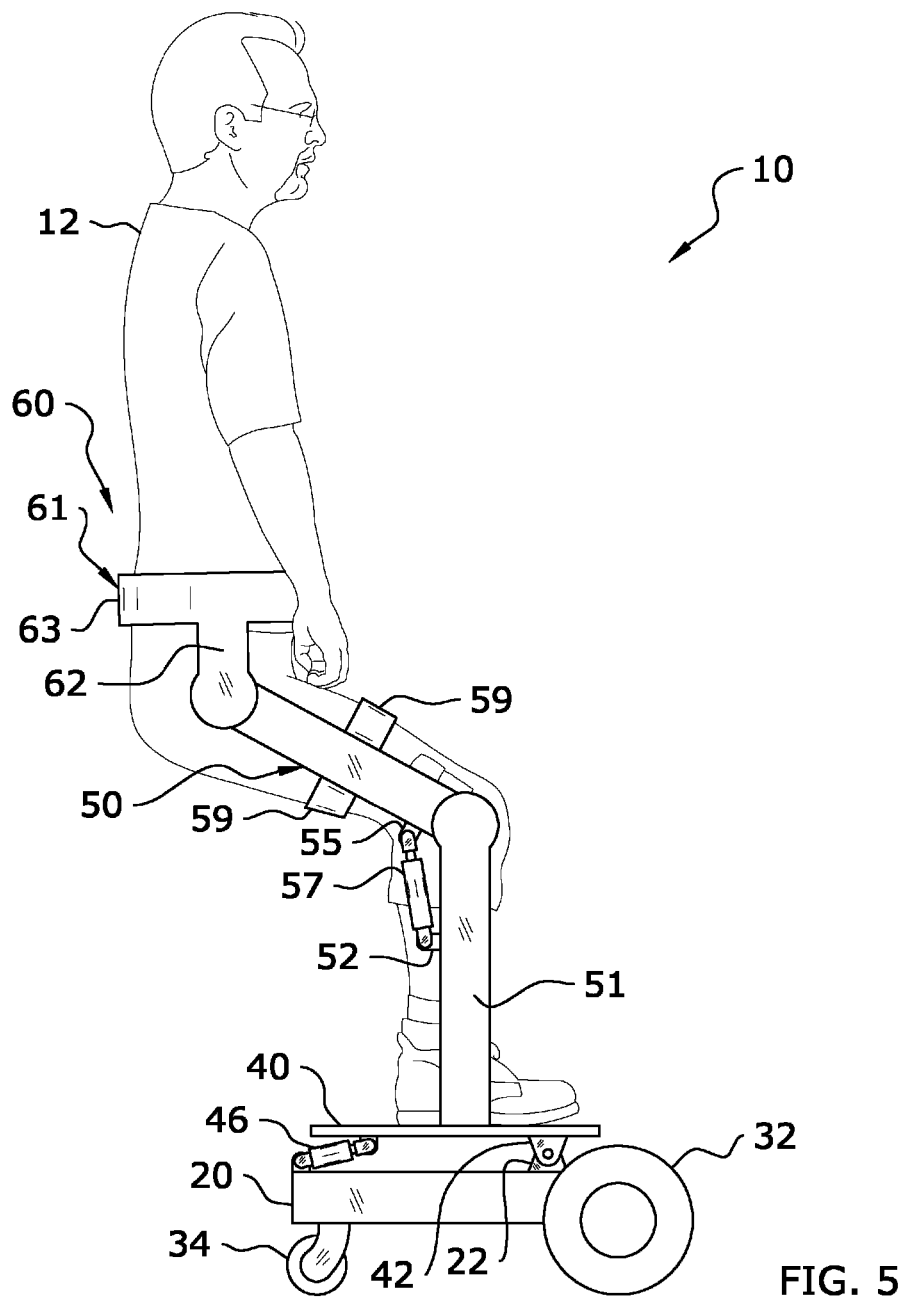
FIG. 5 is a side view of the present invention with a user secured therein and supported in the sitting position.
Figure 6:
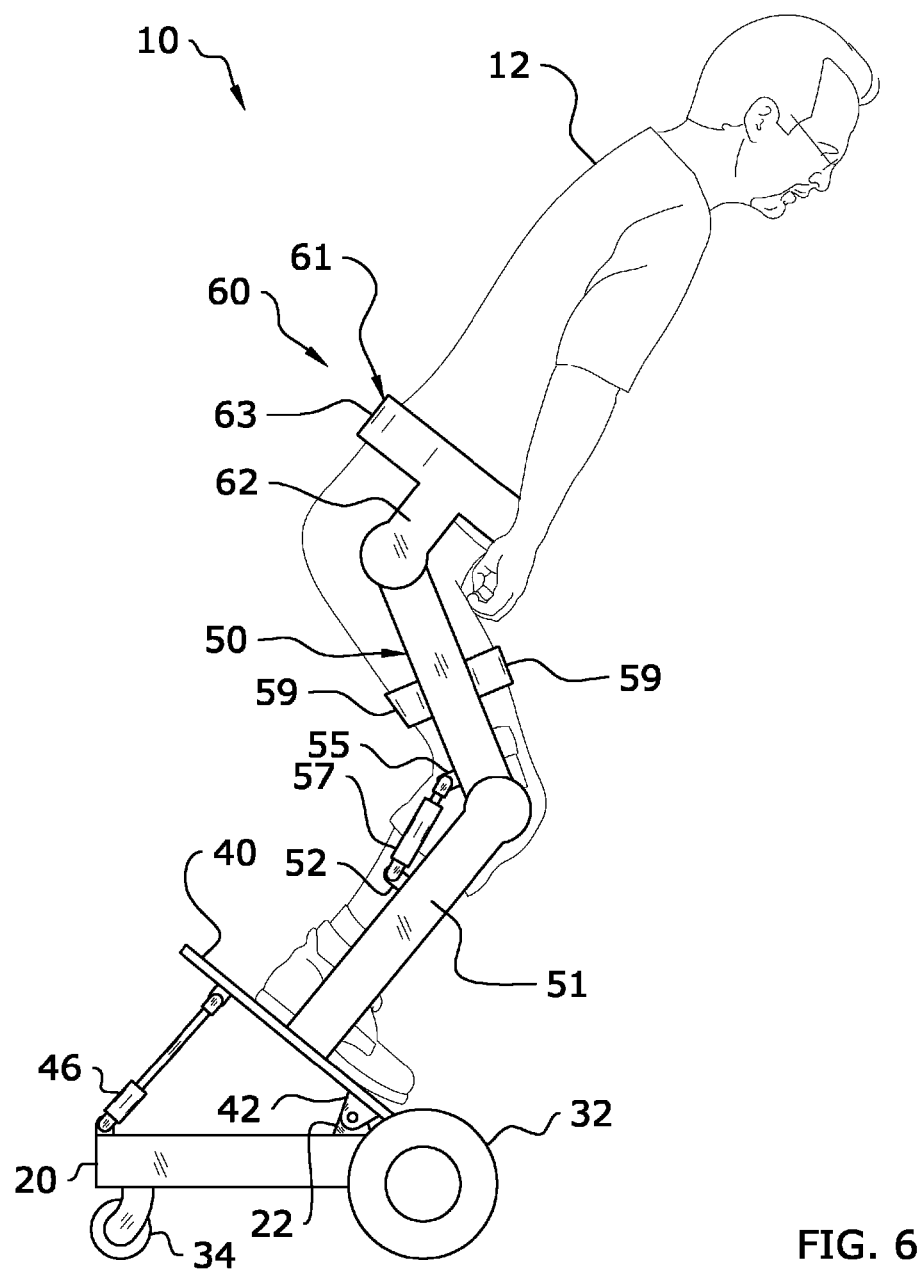
FIG. 6 is a side view of the present invention with a user secured therein and supported in the kneeling position.

The first actuator 46 is connected to the rear of the platform 40 and the rear of the base 20. The first actuator 46 is also able to pivot relative the base 20 and platform 40 to permit for the actuator 46 to extend and retract and thus raise and lower the rear of the base 20 such as to move the platform 40 from a tilted forward position as illustrated in FIG. 6 to a level, horizontal position as illustrated in FIG. 5.

In the preferred embodiment, a lower end of the actuator 46 is connected to the base 20 and an upper end of the actuator 46 is connected to the underside of the platform 40, wherein the upper end extends and retracts from the lower end to pivotally raise and lower the platform 40. Also in the preferred embodiment, the actuator 46 is comprised of a hydraulic cylinder; however it is appreciated that various types of actuators and various numbers of actuators may be used. It is appreciated that in an alternate embodiment of the present invention, the platform 40 may be omitted and the user 12 simply stands upon the top surface of the base 20. Inherently, the leg supporting assemblies 50 would then extend from the base rather than the platform 40.

D. Leg Supporting Assemblies.

The pair of leg supporting assemblies 50 each extends upwards from a respective side of the platform 40. It is appreciated that in alternate embodiments, the leg supporting assemblies 50 may extend upwards from the base 20. Each leg supporting assembly 50 includes an elongated lower segment 51 and an elongated upper segment 54, wherein the upper segment 54 is pivotally connected at a lower end to the upper end of the lower segment 51.

The leg supporting assemblies 50 are spaced apart such as to receive the legs of the user 12 between thereof. It is appreciated that the (first and second) leg supporting assemblies 50 parallel the legs of the user 12 both in the sitting, standing, and kneeling position and may include adjustable leg straps 59 for securing the legs of the user 12 to the upper segment 54 and lower segment 51 of the leg supporting assemblies 50. The leg straps 59 may extend from the lower segment 51 and/or the upper segment 54 to secure the lower or upper portion of the legs of the user 12.

The lower segment 51 includes a lateral support 52 extending rearwardly from thereof and the upper segment 54 includes a lateral support 55 extending rearwardly from thereof. Each of the lateral supports 52, 55 receives a respective lower or upper end of an actuator 57 to pivotally adjust the upper segment 54 with respect to the lower segment 51. It is appreciated that the lower segment 51 is generally in a fixed vertical position relative the platform 40 and does not adjust.

As the (second and third) actuators 57 move to an extended position the upper segment 54 is moved to a vertical position and in-line with the lower segment 51. As the actuators 57 move to a retracted position, such as the upper end retracting within the lower end of the actuators 57, the upper end pulls upon the upper segment 54 thus causing the upper segment 54 to pivot rearwardly such as to be rearwardly angled with respect to the lower segment 51 or even perpendicular to the lower segment 51.

Figure 4:
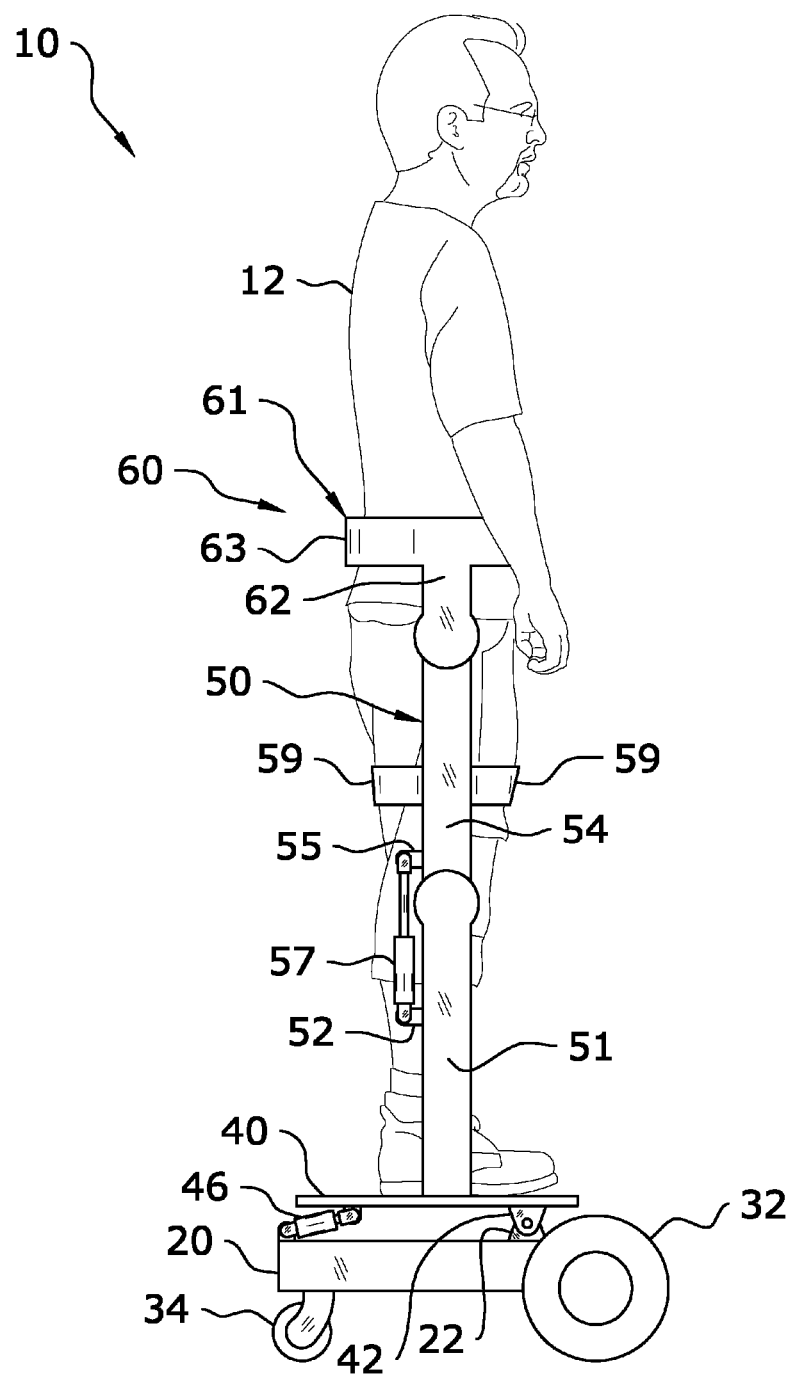
FIG. 4 is a side view of the present invention with a user secured therein and supported in the standing position.

In accordance with the movement of the upper segment 54, the upper part of the legs of the user 12 moves such as to maintain a parallel orientation with the upper segment 54 as illustrated in FIGS. 4 through 6. The actuators 57 also preferably adjust simultaneously so that the upper segments 54 of the pair of leg supporting assemblies 50 adjust simultaneously such as to prevent binding upon the securing assembly 60 and prevent discomfort to the user 12. Also in the preferred embodiment, the actuators 57 are comprised of a hydraulic cylinder; however it is appreciated that various types of actuators and various numbers of actuators may be used.

E. Securing Assembly.

The securing assembly 60 is adapted for securing the user 12 to the mobile device 10 such that the feet of the user 12 are retained atop the platform 40 and the legs of the user 12 remain parallel to the leg supporting assemblies 50. The securing assembly 60 may also retain the back and torso of the user 12 in vertical alignment.

The securing assembly 60 generally comprises a waist support 61 comprised of a generally rigid structure having vertical portions 62 that connect to the upper segments 54 of the leg supporting assemblies 50 and a curved portion 63 that extends along the sides and back of the user 12 adjacent the waist. Extending from the forward end of the curved portion 63 is a waist strap or belt 64 that is detachable and adjustable such as to permit a user 12 to be received by the waist support 61 and to secure the waist of the user 12 therein.

As illustrated in FIG. 3, optionally vertically extending from the waist support 61 is a back support 66 that extends vertically along the back of the user 12 and is T-shaped such as to include a vertical portion 67 and a horizontal portion 68 at the upper end of the vertical portion 67. The vertical portion 67 generally extends along the center of the back and the horizontal portion 68 extends across the shoulder blades. Extending from each end of the horizontal portion 68 are adjustable shoulder straps 69 which retain the torso and back of the user 12 in an upright position against the back support 66.

F. Controller.

Figure 7:
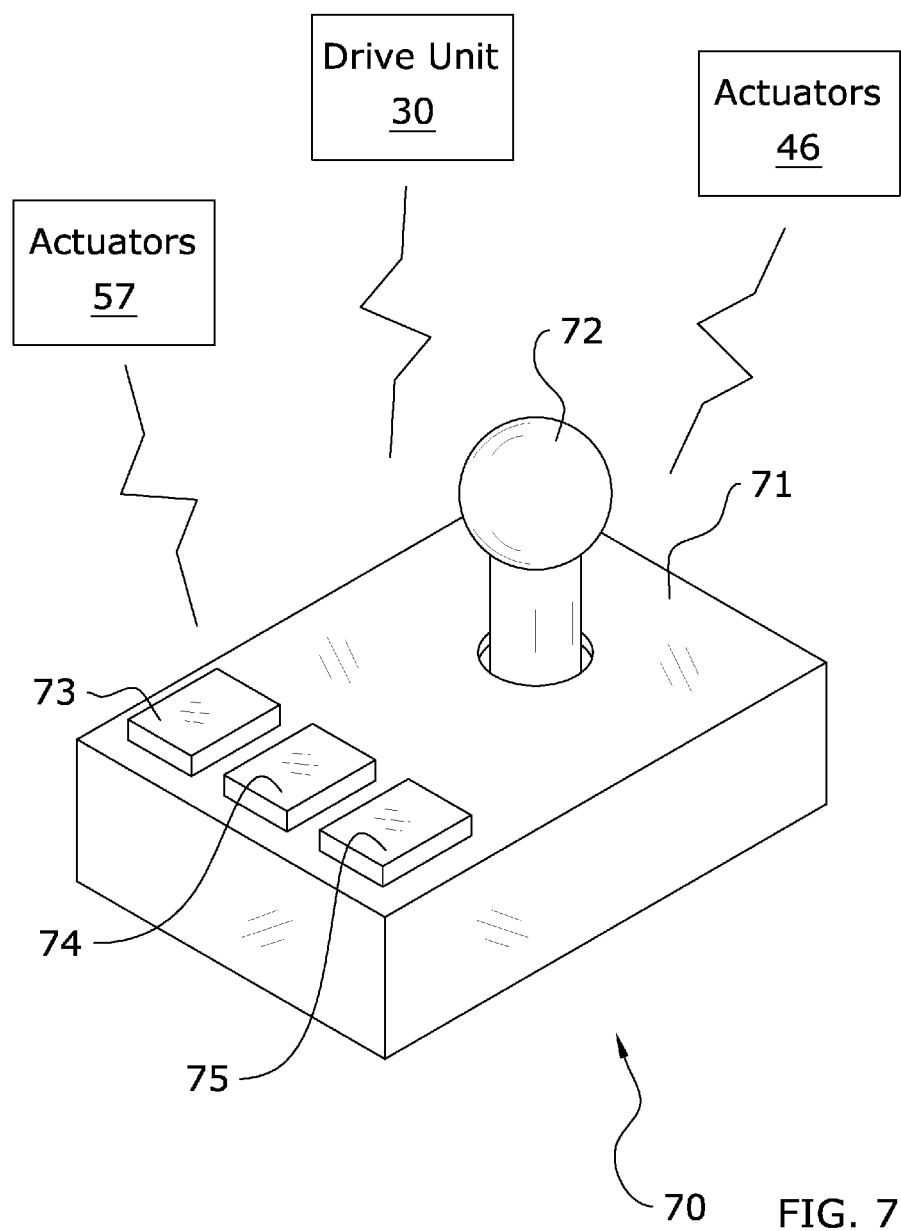
FIG. 7 is an exemplary view of the controller and wireless communication of the controller with the drive unit and actuators.

The mobile device 10 includes a handheld controller 70 for permitting the user 12 to operate the drive unit 30 and actuators 46, 57 as illustrated in FIG. 7. The controller 70 generally includes a small housing 71 such as to be handheld and having internal circuitry, a joystick 72 for controlling the drive unit 30, a first switch or button 73 for controlling the actuators 57 upon the leg supporting assemblies 50, a second switch or button 74 for controlling the actuator 46 connected to the platform 40, and a third switch or button 75 for turning the mobile device 10 on and off.

It is appreciated that the controller 70 and associated controls may have various configurations as appreciated. It is also appreciated that more or less operative controls may be utilized. The controller 70 is generally wireless, such as to wirelessly control the drive unit 30 and actuators 46, 57; however it is appreciated that the controller 70 may be wired to a main control or other master device. It is further appreciated that the drive unit 30 and actuators 46, 57 may each be connected to their power supply, such as batteries, hydraulic source, etc.

G. Operation of Preferred Embodiment.

In use, the feet of the user 12 are positioned upon the platform 40 and the legs of the user 12 are positioned next to each of the leg supporting assemblies 50. In addition, the waist of the user 12 is secured in place via being positioned between the waist support 61 and the waist strap 64 such as illustrated in FIGS. 2 through 6.

The user 12 may operate the joystick 72 of the controller 70 to move the mobile device 10 forward, rearward, left, or right. The user 12 may also operate the actuators 57 of the leg supporting assemblies 50 to pivot the upper segments 54 rearwardly so as to move the user 12 from a standing position as illustrated in FIG. 4 to a sitting position as illustrated in FIG. 5. The platform 40 may also be titled forward to move the user 12 towards a kneeling position as illustrated in FIG. 6 which would permit for the user 12 to pick an item off the floor or kneel.

Unless otherwise defined, all technical and scientific terms used herein have the same meaning as commonly understood by one of ordinary skill in the art to which this invention belongs. Although methods and materials similar to or equivalent to those described herein can be used in the practice or testing of the present invention, suitable methods and materials are described above. All publications, patent applications, patents, and other references mentioned herein are incorporated by reference in their entirety to the extent allowed by applicable law and regulations. In case of conflict, the present specification, including definitions, will control. The present invention may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

The invention claimed is:

1. A mobile device for supporting a user, comprising:
a drivable base having wheels;
a platform pivotally connected to said base, said platform movable from a first position to a second position, said first position being horizontal and said second position being angled forwardly;
a leg supporting means connected to said platform, said leg supporting means being hinged along a lengthwise axis;
an actuating means connected to said leg supporting means, said actuating means adapted to hingedbly move said leg supporting means; and
a securing means connected to said leg supporting means for securing a user such that a feet(s) of the user rests upon said platform and a leg(s) of the user parallels said leg supporting means;
wherein said leg supporting means is comprised of:
a first supporting assembly having a first lower segment and a first upper segment, wherein said first supporting assembly extends from a first side of said platform and wherein said first upper segment is pivotally connected to said first upper segment; and
a second supporting assembly having a second lower segment and a second upper segment, wherein said second supporting assembly extends from a second side of said platform and wherein said second upper segment is pivotally connected to said second upper segment.

2. The mobile device for supporting a user of claim 1, including a second actuating means connected to said platform for pivotally moving said platform between said first position to said second position.

3. The mobile device for supporting a user of claim 2, wherein said second actuating means is comprised of at least one hydraulic cylinder.

4. The mobile device for supporting a user of claim 1, wherein said actuating means is comprised of:
a first actuator having a first lower end and a first upper end, said first lower end being connected to said first lower segment and said first upper end being connected to said first upper segment, wherein said first upper end extends and retracts from said first lower end such as to pivotally adjust said first upper segment with respect to said first lower segment; and
a second actuator having a second lower end and a second upper end, said second lower end being connected to said second lower segment and said second upper end being connected to said second upper segment, wherein said second upper end extends and retracts from said second lower end such as to pivotally adjust said second upper segment with respect to said second lower segment.

5. The mobile device for supporting a user of claim 4, wherein said first actuator and said second actuator are each comprised of hydraulic cylinders.

6. The mobile device for supporting a user of claim 1, wherein said actuating means is comprised of at least one hydraulic cylinder.

7. The mobile device for supporting of claim 1, wherein said securing means is comprised of:
a waist support being comprised of a curved member; and
a strap connected to said waist support for securing a waist of the user between said strap and said waist support.

8. The mobile device for supporting of claim 7, wherein said securing means includes a back support member extending from said waist support and a pair of shoulder straps extending from said back support.

9. The mobile device for supporting of claim 1, including a pair of circulating track members mounted on said wheels of said drivable base.

10. The mobile device for supporting of claim 1, including a controller for operating said drivable base and said actuating means.

11. A mobile device for supporting a user, comprising:
a base having a drive unit and a plurality of wheels, wherein at least some of said plurality of wheels are driven by said drive unit;

a platform pivotally connected to said base, said platform movable from a horizontal position to a forwardly-angled position;

a first actuating means connected to said platform for angular adjustment of said platform between said horizontal position and said forwardly-angled position;

a leg supporting means connected to said platform, said leg supporting means being hinged along a lengthwise axis, wherein said leg supporting means is adjustable from a vertical position to a rearwardly angled position;

a second actuating means connected to said leg supporting means, said second actuating means adapted to hingedbly move said leg supporting means between said vertical position and said rearwardly-angled position;

a securing means connected to said leg supporting means for securing a user such that a feet(s) of the user rests upon said platform and a leg(s) of the user parallels said leg supporting means; and a controller means to operably control said drive unit, said first actuating means, and said second actuating means;

wherein said leg supporting means is comprised of:

a first supporting assembly having a first lower segment and a first upper segment, wherein said first supporting assembly extends from a first side of said platform and wherein said first upper segment is pivotally connected to said first upper segment; and a second supporting assembly having a second lower segment and a second upper segment, wherein said second supporting assembly extends from a second side of said platform and wherein said second upper segment is pivotally connected to said second upper segment.

12. The mobile device for supporting a user of claim 11, wherein said first actuating means is comprised of at least one first hydraulic cylinder and wherein said second actuating means is comprised of at least one second hydraulic cylinder.

13. The mobile device for supporting a user of claim 10, wherein said second actuating means is comprised of:

a first actuator having a first lower end and a first upper end, said first lower end being connected to said first lower segment and said first upper end being connected to said first upper segment, wherein said first upper end extends and retracts from said first lower end such as to pivotally adjust said first upper segment with respect to said first lower segment; and a second actuator having a second lower end and a second upper end, said second lower end being connected to said second lower segment and said second upper end being connected to said second upper segment, wherein said second upper end extends and retracts from said second lower end such as to pivotally adjust said second upper segment with respect to said second lower segment.

14. The mobile device for supporting a user of claim 13, wherein said first actuator and said second actuator are each comprised of hydraulic cylinders.

15. The mobile device for supporting of claim 11, wherein said securing means is comprised of:

a waist support being comprised of a curved member; and a strap connected to said waist support for securing a waist of the user between said strap and said waist support.

16. The mobile device for supporting of claim 11, wherein said securing means includes a back support member extending from said waist support and a pair of shoulder straps extending from said back support.

17. The mobile device for supporting of claim 11, including a pair of circulating track members mounted on said plurality of wheels of said base.

18. A mobile device for supporting a user, comprising:

a base having a drive unit and a plurality of wheels, wherein at least some of said plurality of wheels are driven by said drive unit;

a platform pivotally connected to said base, said platform movable from a horizontal position to a forwardly-angled position;

at least one first actuator connected to said platform for angular adjustment of said platform between said horizontal position and said forwardly-angled position;

a leg supporting means connected to said platform, said leg supporting means being hinged along a lengthwise axis, wherein said leg supporting means is adjustable from a vertical position to a rearwardly angled position;

wherein said leg supporting means is comprised of a first supporting assembly having a first lower segment and a first upper segment, wherein said first supporting assembly extends from a first side of said platform and wherein said first upper segment is pivotally connected to said first upper segment, and a second supporting assembly having a second lower segment and a second upper segment, wherein said second supporting assembly extends from a second side of said platform and wherein said second upper segment is pivotally connected to said second upper segment;

wherein each supporting assembly includes at least one leg strap;

a second actuator being connected to said first lower segment and said first upper segment such as to pivotally adjust said first upper segment with respect to said first lower segment between said vertical position and said rearwardly-angled position;

a third actuator being connected to said second lower segment and said second upper segment such as to pivotally adjust said second upper segment with respect to said second lower segment between said vertical position and said rearwardly-angled position;

wherein said second actuator and said third actuator adjust at the same time;

a securing means connected to said leg supporting means for securing a user such that a feet(s) of the user rests upon said platform and a leg(s) of the user parallels said leg supporting means;

wherein said securing means is comprised of a waist support being comprised of a curved member, a strap connected to said waist support for securing a waist of the user between said strap and said waist support, a back support member extending from said waist support, and a pair of shoulder straps extending from said back support; and a wireless hand-held controller to operably control said drive unit, said first actuator, said second actuator, and said third actuator.

* * * * *